United States Patent [19]

Minami et al.

[11] Patent Number: 5,218,971
[45] Date of Patent: Jun. 15, 1993

[54] APPARATUS FOR AUTOMATICALLY MEASURING A QUANTITY OF URINE

[75] Inventors: Yoshiteru Minami, 1-6-3, Hayamiya, Nerima-ku, Tokyo; Kazuhiro Oya, Kunitachi, both of Japan

[73] Assignees: Stec Inc., Kyoto; Yoshiteru Minami, Tokyo, both of Japan

[21] Appl. No.: 782,417

[22] Filed: Oct. 25, 1991

[30] Foreign Application Priority Data

Oct. 27, 1990 [JP] Japan ................... 2-290506

[51] Int. Cl.⁵ ............................................. A61B 5/00
[52] U.S. Cl. ..................................... 128/771; 128/760; 235/375; 4/304
[58] Field of Search ............... 128/760, 761, 762, 771; 40/1.5, 1.6, 625, 633; 382/2, 64; 4/144.1, 302, 304, 305, 301, 340, 341, 342; 235/380, 382, 493, 375

[56] References Cited

U.S. PATENT DOCUMENTS

| 3,683,894 | 8/1972 | Villari | 128/771 |
|---|---|---|---|
| 3,888,236 | 6/1975 | Marx | 128/771 |
| 4,002,075 | 1/1977 | Cross | 73/426 |
| 4,164,320 | 8/1979 | Irazoqui et al. | 235/375 |
| 4,305,405 | 12/1981 | Melsch | 128/762 |
| 4,575,880 | 3/1986 | Burgess | 4/313 |
| 4,753,249 | 6/1988 | Muller | 128/771 |
| 4,779,120 | 10/1988 | Haas | 355/40 |
| 4,793,588 | 12/1988 | Laverty, Jr. | 251/30.03 |
| 4,961,431 | 10/1990 | Ikenaga et al. | 128/760 |
| 5,063,955 | 11/1991 | Sakakibara | 137/1 |
| 5,078,012 | 1/1992 | Ding et al. | 73/861.74 |

FOREIGN PATENT DOCUMENTS

| 0052495 | 5/1982 | European Pat. Off. . |
| 0308080 | 3/1989 | European Pat. Off. . |
| 0393784 | 10/1990 | European Pat. Off. . |
| 3541649A1 | 6/1987 | Fed. Rep. of Germany . |

Primary Examiner—Max Hindenburg
Assistant Examiner—Guy V. Tucker
Attorney, Agent, or Firm—Price, Gess & Ubell

[57] ABSTRACT

A system for automatically measuring a quantity of urine from a plurality of individuals is provided wherein a common urinal can act as both a receptacle for measuring urine from a designated patient and for exhausting the urine in the normal disposal system. A weight scale can measure the amount of urine when appropriate valves are activated as a result of the identification system that can recognize a badge on the individual. A computer system can store data on the quantity of urine measured and can activate valves to dispose of the measured urine.

8 Claims, 4 Drawing Sheets

Fig. 4

| NO | 0001 | 0002 | 0003 | 0001 | 0005 |
|---|---|---|---|---|---|
| NAME | ○○○○ | ××※× | □□□□ | △△△△ | ○×□△ |
| DATA 1 | 07:15 333.6 | 06:12 286.3 | 06:43 285.0 | 09:27 319.5 | 05:48 298.3 |
| DATA 2 | 10:22 256.0 | 09:58 198.3 | | | 09:22 299.3 |
| DATA 3 | | 12:36 345.0 | | | |
| DATA 4 | | | | | |
| DATA 5 | | | | | |
| DATA 6 | | | | | |
| DATA 7 | | | | | |
| DATA 8 | | | | | |
| DATA 9 | | | | | |
| DATA 10 | | | | | |
| TOTAL | 594.6 | 829.6 | 285.0 | 319.5 | 597.6 |

APPARATUS FOR AUTOMATICALLY MEASURING A QUANTITY OF URINE

BACKGROUND OF THE INVENTION

1. Field of the Invention

The present invention relates to a novel, useful, automatic urine-measuring apparatus for determining the quantity of urine passed by an individual.

2. Description of Related Art

In general, hospitals have collected urine in a container, such as a urinal, in order to determine a quantity of urine discharged from a patient for a one-day time period.

However, the following problems have occurred in the above-described collection of urine. A large space for keeping containers, such as urinals, with the name of a person who discharged the urine, such as a patient, marked thereon, is required in a lavatory. In addition, since a plurality of containers must be stored, a disagreeable odor can be generated around the laboratory, and an unsanitary condition can be created. Furthermore, even though a person in charge, such as a nurse, measures the quantity of urine within the respective containers once a day, a problem has occurred in that considerable time and labor are required.

SUMMARY OF THE INVENTION

The present invention has been achieved paying attention to the above-described matters, and it is an object of the present invention to provide a novel, useful automatic urine-measuring apparatus capable of automatically measuring a quantity of urine discharged from a specified person, such as a patient, without requiring a large space, creating a disagreeable odor, and causing concern to the medical staff.

The urine-measuring apparatus of the present invention includes a stool or urinal in which the urine is deposited, a weight-measuring portion provided in the scupper of the urinal, a discriminating sensor for discriminating the identity of the person standing in front of the urinal, and a control system for recording the quantity of urine discharged and identifying that quantity with a specific individual patient who has been previously entered into the control system.

In operation, the individual, e.g., the patient, can be provided with a magnetic identification ("ID") card that can be attached to a portion of his body, such as his hospital gown. This ID card can be sensed by a sensor that can be controlled by a CPU system. When the patient stands in front of the urinal, a microwave discriminating device attached adjacent the urinal can discriminate the identity of the patient, and a valve can be closed, to thereby store the quantity of urine deposited in the urinal by the patient. After the measurement has been determined and recorded, a closing valve is then opened to discharge the urine into an exhaust passageway. The actual measured quantity of urine that has been deposited into the scupper, along with the identification data sensed by the CPU system, can be recorded. Thus, the name of the person discharging the urine, the time period of the urine discharge, and the quantity, e.g., in cubic centimeters, can be recorded. This information, such as the quantity of urine over a predetermined time period, can be summed up, and a determination of any abnormality by comparison with a suitable value that has been prestored in the memory of the CPU system, can be carried out. The data that is input into the memory of the CPU system can also be printed out or displayed on a display panel, as the occasion demands, and can obviously be used as reference material for medical treatment of the patient and as a pathological investigation.

In those cases where a patient, or a layperson who is not a patient, utilizes the urinal by standing in front of it without a magnetic ID card, a determination can be made that he is not one of the predetermined persons for whom the system is to record information. Accordingly, the closing valve is not closed, and the urine is discharged directly into the exhaust passage without being measured. In essence, the urinal functions as a normal urinal is expected to function.

BRIEF DESCRIPTION OF THE DRAWINGS

FIGS. 1-4 show one preferred embodiment of the present invention, wherein:

FIG. 1 is a diagram schematically showing the construction of an automatic urine-measuring apparatus according to the present invention;

FIG. 2 is a partial cross-sectional configuration of a urine-measuring portion of the system;

FIG. 3 is a schematic block diagram showing the control relationship of the urine-measuring apparatus; and FIG. 4 is a diagram showing one example of recorded data that be printed out from the CPU system.

DESCRIPTION OF THE PREFERRED EMBODIMENTS

The preferred embodiments of the present invention will be given below with reference to the drawings.

Figure 1:
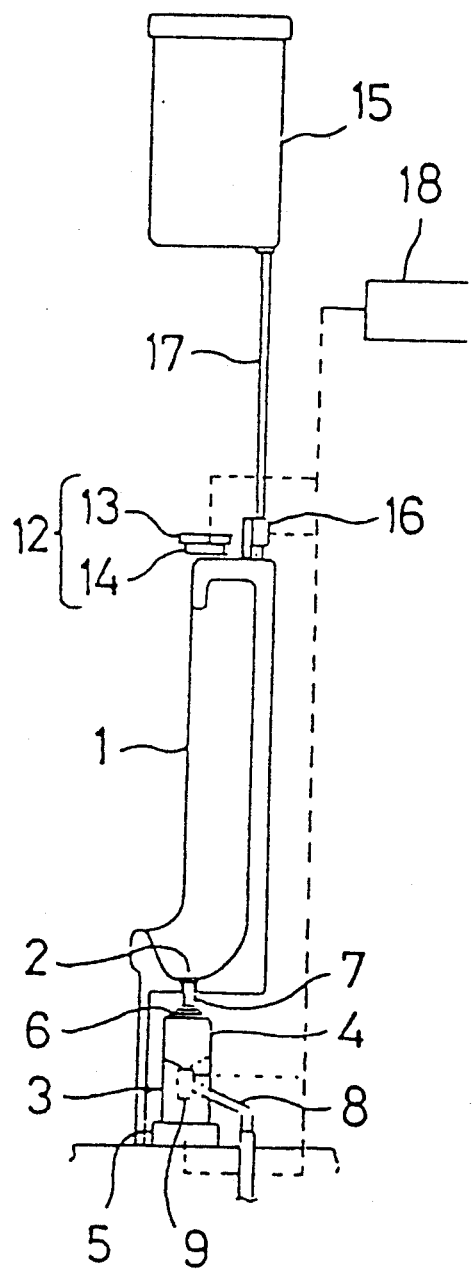
Figure 2:
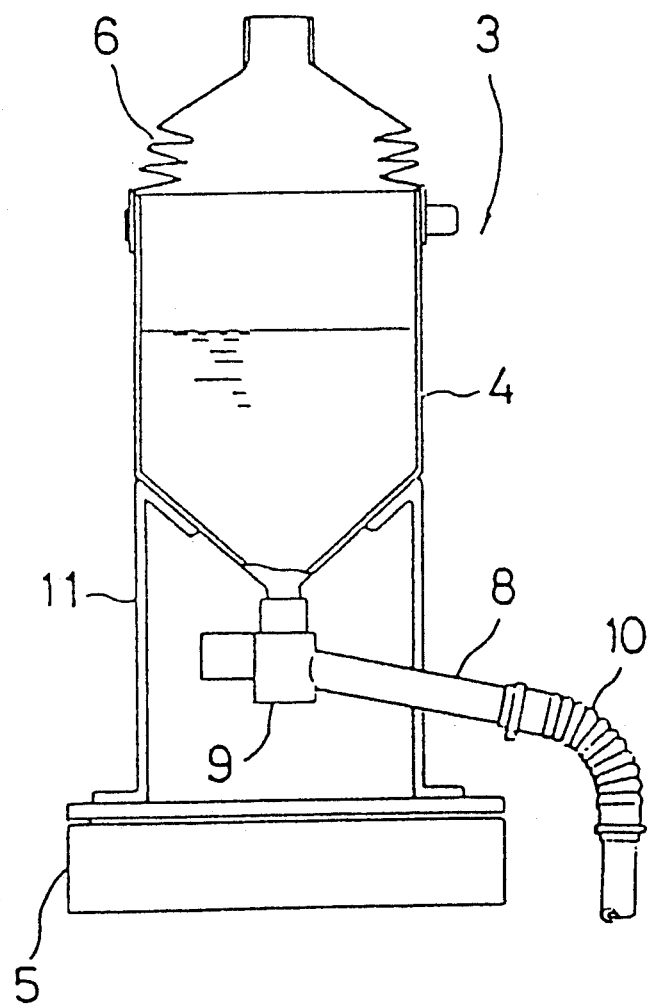

One preferred embodiment of the present invention is shown in FIGS. 1-4. FIG. 1 is a diagram schematically showing the construction of an automatic urine-measuring apparatus according to the present invention. Referring to FIG. 1, reference numeral 1 designates a stool or urinal provided with a urine-measuring portion 3 disposed below a scupper 2 thereof. The urine-measuring portion 3 comprises a common receptacle or measuring container 4 and an electronic balance 5 for receiving the measuring container 4 thereon to measure it. An upper portion of the measuring container 4 is formed of a bellows portion 6 which communicates with a drain pipe 7 hanging down from the scupper 2. In addition, a bottom portion of the measuring container 4 communicates with a drain pipe 8. The drain pipe 8 is provided with a closing valve 9, such as an electromagnetic valve, and a flexible pipe 10 to which its downstream side is connected with an exhaust passage (not shown). Furthermore, reference numeral 11 designates a support member for stably supporting the measuring container 4.

Reference numeral 12 designates a discriminating portion or sensor disposed in the vicinity of the urinal 1, for example, above the urinal 1, and comprising a human body-detecting sensor 13, such as an infrared sensor, and a microwave discriminating device 14 for discriminating whether or not a person standing in front of the urinal 1 to discharge urine is a predetermined specified person. Reference numeral 15 designates a water tank connected with an upper portion of the urinal 1 through a supply pipe 17 provided with a closing valve 16, such as an electromagnetic valve, for storing water for washing the urinal.

Figure 3:
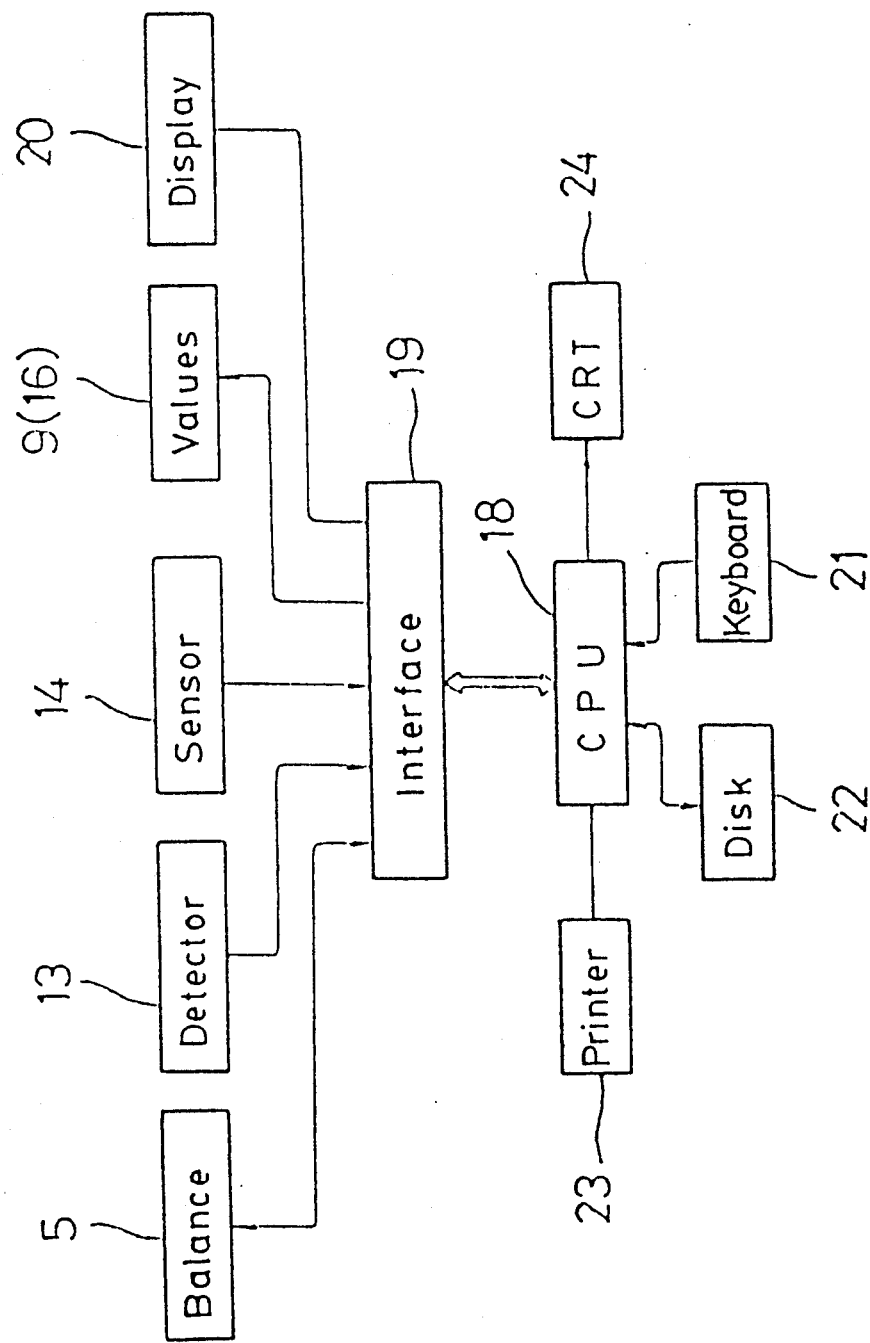

FIG. 3 schematically shows a computer-based control system in an automatic urine-measuring apparatus having the above-described construction. Referring to FIG. 3, reference numeral 18 designates a CPU circuit as a control portion that is respectively connected with not only the electronic balance 5, the human body-detecting sensor 13, the microwave discriminating device 14, the closing valve 9, the closing valve 16, and the use of a display lamp 20 through an I/O interface circuit 19, but also a keyboard 21 as an input device, a disk 22 for inputting data into the system, a printer 23 as an output device, and a CRT 24 as a display. The CPU 18 processes data on the basis of input from the electronic balance 5 to control the various sequences of operation that not only includes the result of storing the information sensed and operated upon in a memory disk 22, displaying it on the CRT 24, or outputting it by means of the printer 23, but also to controlledly open and close the closing valves 9, 16 on the basis of a signal from the human body-detecting sensor 13 and the microwave discriminating device 14.

An operation of the automatic urine-measuring apparatus having the above-described construction will be described below.

Provided that a specified person, such as a subject patient whose quantity of urine is to be measured, is equipped with a magnetic ID card (not shown) which is readable by receipt of microwaves when placed on a part of the patient's body, for example, a breast, the name of the specified person is registered or stored in the CPU 18 in advance, together with various classification codes (sex distinction, attachment, specified code number and the like). When the patient equipped with such a magnetic ID card or personal identification apparatus stands in front of the urinal 1, the human body-detecting sensor 13 provided above the urinal 1 not only detects the start of a use of the urinal 1, but also discriminates, by means of the microwave discriminating device 14, that the person standing in front of the urinal 1 has been previously entered into the system as a patient, whereby an appointed discriminating signal is set in the CPU 18. An appointed signal from the CPU 18 on the basis of the above-described input immediately closes the closing valve 9 of the urine-measuring portion 3, whereby collecting all of the urine discharged by the patient into the measuring container 4. Since a measured value by the electronic balance 5 when the measuring container 4 is empty is different from that when the urine is collected within the measuring container 4, the difference is measured as the weight of the urine, and a measured output at this time is sent to the CPU 18.

When the patient leaves the front of the urinal 1, the completion of the use of the urinal 1 is detected, and valve 9 and valve 16 are subsequently opened on the basis of a signal from the CPU 18, thereby discharging the urine within the measuring container 4 into an exhaust passage, and opening the valve 16, to supply the urinal 1 with water from the tank 15 to conduct a washing of the surface of the urinal 1.

The measured output from the urine-measuring portion 3 is transformed into a volume value (cc) by the known value of a specific gravity of urine in the CPU 18 to be recorded as data in a format, as shown in FIG. 4, together with a urine-discharging time for every patient. As understood from FIG. 4, the measured result is obtained in the CPU 18 together with the ID data for every registered specified person, such as a patient, to be stored so that the urine-discharging time, and the quantity of urine for every urine-discharging time, can be totaled and supplied to the operator. In addition, a judgment of any abnormalities can be accomplished by a comparison with predetermined values which may be entered as occasion demands. These data are housed in the disk 22. The housed data can be printed out by the printer 23 or displayed on the CRT 24, as occasion demands, to be used as reference materials for medical treatment of the patient and a pathological investigation.

In the case when a patient or other person, without a magnetic ID card, stands in front of the urinal 1, the human body-detecting sensor 13 provided on the urinal 1 detects the start of a use of the urinal 1, but an appointed discriminating signal is not output from the microwave discriminating device 14, so that the closing valve 9 of the urine-measuring portion is not closed and the urine is discharged into the exhaust passage without being measured. As soon as the person leaves the front of the urinal 1, the completion of the use of the stool 1 is detected to open the closing valve 16 on the basis of a signal from the CPU 18, whereby washing the urinal 1 with wash water from the tank 15. In summary, the urinal 1 can function as a standard urinal in this event.

The present invention is not limited by the above-described preferred embodiment. For example, the measurement of urine may be conducted by a method of using a liquid level indicator and also by a method of using a liquid flow meter in place of the above weight balance. For example, in the case of a method using a liquid level indicator, an ultrasonic system, a laser system, and the like can be adopted for the detection of a liquid level. Additionally, an impeller-type of flow meter and the like could be used as the liquid flow meter to simplify the construction of the urine-measuring portion 3.

A designated person may be equipped with a microwave oscillator in place of the above-described magnetic ID card as the discriminating means for discriminating whether the urine-discharging person is a qualified person, whether registered in advance or not.

The automatic urine-measuring apparatus may be provided in a plurality of urinals 1 that are jointly controlled by the CPU 18.

The present invention having the above-described construction features eliminates the space requirements necessary for keeping a plurality of containers, and also eliminates the sanitary and odor problems that have been an issue in the past. As can be readily appreciated, the present invention can be integrated into a conventional urinal bowl so that present systems can be retrofitted to accommodate the purposes of the present invention.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A system for automatically measuring a quantity of urine from a plurality of individuals, comprising:
   a measuring container for receiving urine from the plurality of individuals;
   a valve member connected to the measuring container for controlling the draining of the measuring container;

a plurality of personal identification apparatus, for specifically identifying each individual, which is capable of being transported with each individual;

identification means for directly interacting with the personal identification apparatus to automatically identify the individual who is transporting a personal identification apparatus;

measuring means for selectively measuring the quantity of urine deposited in the measuring container;

control means, responsive to the identification means, for controlling the valve member to prevent drainage and to activate the measuring means to measure the quantity of urine;

means for storing data on the quantity of urine measured relative to the indentified individual; and means for disposing of each quantity of measured urine when the measuring means has finished its operation and the individual removes himself or herself from adjacent the measuring container.

2. The invention of claim 1 wherein the means for storing data on the quantity of urine measured further includes a computer system that can store time-related information on the depositing of the urine.

3. The invention of claim 2 wherein the means for disposing of each quantity of measured urine includes a human body infrared detecting sensor and a valve for controlling a release from the measuring container.

4. The invention of claim 3 wherein the computer system can sum the total depositing of urine over several measurements for a predetermined period of time for an individual.

5. The invention of claim 4 wherein the computer system can compare the quantity of measured urine with a reference value to determine an abnormal condition.

6. The invention of claim 4 wherein the measuring container is attached to a urinal.

7. The invention of claim 6 wherein the measuring means includes a weight measuring instrument for measuring the weight of the quantity of urine.

8. The invention of claim 7 wherein the personal identification apparatus includes a magnetic identification card capable of being worn by the individual.

* * * * *